United States Patent [19]

Reger et al.

[11] Patent Number: 4,972,351

[45] Date of Patent: Nov. 20, 1990

[54] COMPUTER AIDED FABRICATION OF WHEELCHAIR SEATS OR OTHER BODY SUPPORTS

[75] Inventors: Steven I. Reger, Shaker Heights; Donald C. Neth, Parma; Thomas F. McGovern, Cleveland Heights, all of Ohio

[73] Assignee: The Cleveland Clinic Foundation, Cleveland, Ohio

[21] Appl. No.: 297,888

[22] Filed: Jan. 17, 1989

Related U.S. Application Data

[63] Continuation-in-part of Ser. No. 219,606, Jul. 14, 1988, Pat. No. 4,890,235.

[51] Int. Cl.⁵ .............................................. G06F 15/46
[52] U.S. Cl. .................................. 364/468; 364/473; 364/413.01; 364/579; 297/458; 297/DIG. 4; 264/222; 264/313
[58] Field of Search ............... 364/468, 473, 413.01, 364/579; 297/458, DIG. 4; 264/222, 313-316

[56] References Cited

U.S. PATENT DOCUMENTS 4,637,789  1/1987  Netznik ............................ 264/316
4,828,325  5/1989  Brooks ............................. 297/458

OTHER PUBLICATIONS

S. I. Reger, et al., Shape and Pressure Distribution on Wheelchair Cushions, pp. 341-343, (1985).
S. I. Reger, et al., Instrumented, Adjustable Seat for Evaluating Posture and Body Contours, pp. 335-337, (1985).
D. A. Hobson, Research and Development Considerations and Engineering Perspective, pp. 122-129, (1986).
S. I. Reger, et al., Weightbearing Tissue Contour and Deformation by Magnetic Resonance Imaging, pp. 387-389, (1986).
G. W. McGrew, et al., Clinical Application of the Adjustable "Computer Chair", pp. 568-570, (1987).
K. C. Chung, et al., Comparative Evaluation of Pressure Distribution of Flat Foams, etc., pp. 323-325, (1987).
K. C. Chung, et al., Body Contours and Pressure Distributions of Normal and Sci Subjects, etc., pp. 515-517, (1987).
K. C. Chung, et al., Analysis of Compression, Shear and Surface Tension on Seat Cushions, pp. 269-271, (1987).
D. M. Brienza, et al., Design of a Computer Aided Manufacturing System for Custom Contoured Wheelchair Cushions, pp. 312-313, (1988).
K. C. Chung, et al., Effect of Contoured Support Surface on Pressure Distribution, pp. 314-315, (1988).
O. Nwaobi, et al., Hip Angle and Upper Extremity Movement Time in Children with Cerebral Palsy, pp. 39-41, (1985).
S. I. Reger, et al., Computer Aided Prescription of Specialized Seats for Wheelchairs (Aug. 31, 1987).

Primary Examiner—Allen MacDonald
Attorney, Agent, or Firm—Fay, Sharpe, Beall, Fagan, Minnich & McKee

[57] ABSTRACT

A system is provided for generating prescription wheelchair seats or specialized seating or body supports. The system includes a deformable seat portion which is formed to specialized dimensions of a seated patient. A planar, linear, array of linear transducers is stepped across the form in one dimension forming a series of signals representative of generally planar cross sections of the form. This series of cross-sectional signals is provided as an input to a numerically controlled cutting device which cuts a series of sheet stock foam in accordance with each cross-sectional area measured. These cross-sectional pieces are then assembled into the prescription seat.

20 Claims, 2 Drawing Sheets

COMPUTER AIDED FABRICATION OF WHEELCHAIR SEATS OR OTHER BODY SUPPORTS

This is a continuation-in-part of copending applications Ser. No. 219,606 filed on July 14, 1988, now U.S. Pat. No. 4,890,235.

BACKGROUND OF THE INVENTION

This application pertains to the art of fabrication of specialized seating, and more particularly to computer aided and numerically controlled seat design and fabrication.

The invention is particularly applicable to fabrication of prescription wheelchair seating and will be described with particular reference thereto. It will be appreciated, however, that the invention has broader applications such as in fabrication of beds, seating units, foot support, or the like.

It is estimated that more than 45 million people in the United States are affected by disabilities which impair their mobility. One common method used to overcome such disabilities is use of wheelchairs. The number of daily wheelchair users exceeds 0.75 million people.

Disabled individuals often spend considerable time a wheelchair. Accordingly, and interface between the individual and the wheelchair is crucial. Without an accurate fit of the support system, pressure sores and postural deformity may result. Expenses for treatment of pressure sores and deformities are extremely high, and are increasing. Estimates of the costs associated with the healing of pressures sores in 1978 were given to be between $10,000 and $46,000. More recently, the range is shown to have widened to be from $3,400 to $86,000 with an increase of the mean costs of nearly $10,000.

When chosen correctly, cushions and body supports can be effective in reducing the risk of pressure sores and for maintaining postural alignment. The subject of wheelchair cushion prescription is well documented in the literature. Various methods of selection, testing, and determination of specialized characteristics, have been described. Even when acceptable, individualized, seating dimensions have been decided upon, fabrication of a wheelchair bearing the appropriate seating dimensions must be accomplished.

Presently, typical fitting and fabrication for prescription wheelchair seating is accomplished by what is referred to as the "dilatency casting method," which is described as follows. A patient is seated on a wheelchair form which generally includes a horizontal portion pivotally connected to a vertical portion. Various orientations of the horizontal and vertical sections are generally made. Contiguous with both the horizontal and vertical sections are "bean-bag" padding sections, the cover of which is airtight.

A patient is seated on the form. An acceptable vertical orientation of the vertical portion is made, as is an acceptable horizontal orientation of the horizontal portion. A shaping of the cushions is undertaken to provide an acceptable force distribution along the portions of the seat contacting the patient. After this has been accomplished, air from the cushions is evacuated, thus forming a semi-rigid seat which matches an acceptable contour.

Next, a casting, such as a powdered gypsum plaster of paris casting, is made of the selected seat contour. After hardening, this casting is carefully boxed and shipped to a seat manufacturer.

A seat manufacturer, upon receipt of the casting, undertakes a series of measurements of various cross-sections thereof. This cross-sectional information is used by a machinist to hand-cut sheet stock to the approximate dimensions of a measured cross-section. Individual cut portions of sheet stock are trimmed and refined until they closely approximate a cross-sectional portion of the form from which the casting was made.

After this time, a second cross-sectional measurement is taken at a distance from the preceding one, which distance is dictated by the thickness of the sheet stock being used for fabrication. This process is repeated for the entire casting.

Upon completion of cutting of all sheet stock portions, they are secured to one another to form a seat cushion resembling, as closely as possible, the casting. Given that discrete sheet portions have been used to fabricate the seat, rough corners between the various sections must be smoothed to acceptable tolerances.

It is apparent that the above-noted procedure, while often yielding acceptable seating, is a laborious, time consuming, and accordingly, expensive. Delays are experienced which are resultant from time necessary to prepare the casting, time necessary to ship the casting to a manufacturing location, and time necessary to manually measure, cut, refine, trim, and assemble, the series of sheet stock from which the support is manufactured. In addition, castings are susceptible to breakage, and introduce added error potential into the manufacturing process. Presently, fabrication of seating with the above procedure requires investment of several thousands of dollars, and several months in time.

In addition to the time and expense associated with the above-described manufacturing process, a patient must accept problems associated with improper seating for extended periods while he or she awaits receipt of the completed prescription seat. Such delays may find a patient with physiological characteristics altered due to improper seating during the wait.

The present invention contemplates a new and improved system for achieving a personalized support system which overcomes all of the above-referred problems, and others, and provides a system for arriving at a prescription support efficiently, economically, and with improved accuracy.

SUMMARY OF THE INVENTION

In accordance with the present invention, there is provided a contoured support fabrication unit which includes a form which defines an individualized contour. A sensing means senses a cross-sectional shape along first and second dimensions of the form, and generates a signal representative thereof. After such a signal has been acquired, the sensing means is incremented along the form, and a subsequent reading is taken.

In accordance with a more limited aspect of the present invention, the sensing means is comprised of a plurality of linear transducers, each of which is displaceable along its longitudinal axis. The linear transducers are secured in a generally linear array such that each longitudinal axis is generally parallel to one another.

In accordance with a still more limited aspect of the present invention, a means is provided for obtaining a series of cross-sectional signals from selected displacements of the sensing means along a dimension of a form means.

In accordance with a yet more limited aspect of the present invention, the cross-sectional information is communicated to a means for fabricating a seat.

In accordance with a yet still more limited aspect of the present invention, the fabrication means is comprised of a numerically-controlled means for cutting sheet stock from which a completed seat is assembled.

In accordance with another aspect of the present invention, a method is provided for forming a prescription seat in conjunction with the above apparatus.

An advantage of the present invention is the provision of the system with which a prescription body support member may be more accurately fabricated.

Another advantage of the present invention is the provision of a system for substantially decreasing the time necessary for fabricating a prescription body support.

Yet another advantage of the present invention is the provision of a system by which a prescription support system may be defined remotely from the fabrication unit, with electronic communication of contour data therebetween.

Further advantages will become apparent to one of ordinary skill in the art upon reading and understanding of the subject specification.

DESCRIPTION OF THE DRAWINGS

The present invention may take physical form in certain parts and arrangements of parts, a preferred embodiment of which will be described in detail in the specification and illustrated in the accompanying drawings which forms a part hereof, and wherein.

DETAILED DESCRIPTION OF THE PREFERRED EMBODIMENT

Figure 1:
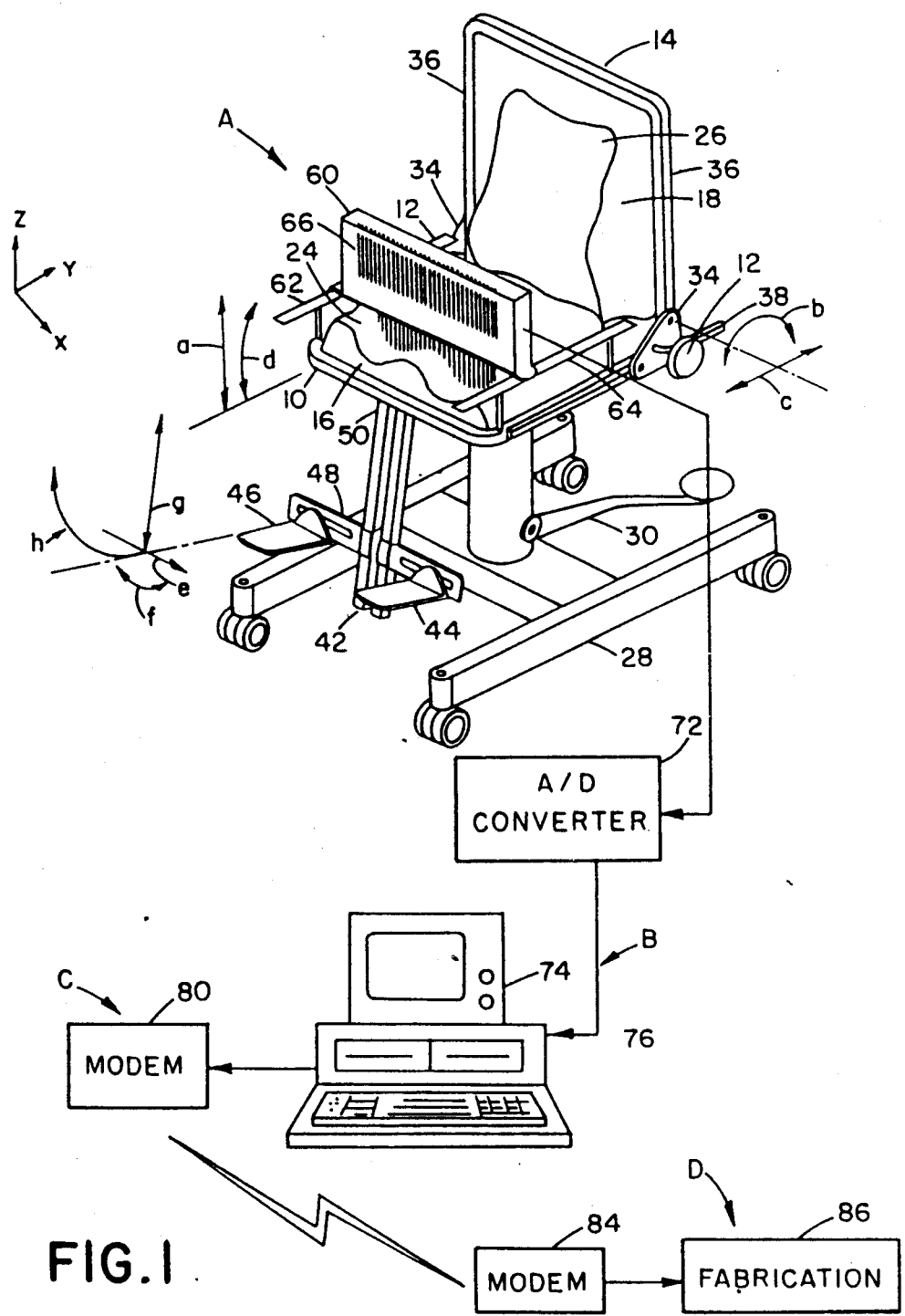
FIG. 1 is a schematic representation of a prescription wheelchair seat system in accordance with the present invention.

Referring now to the drawings wherein the showings are for the purposes of illustrating the preferred embodiment only, and not for the purposes of limiting the same, FIG. 1 illustrates a fitting seat or form means A which is in data communication with a computer means B, which computer means is in turn in data communication through a communication interface C to a manufacturing location D.

The subject system provides a means and method for formation of customized body supports. It will be described with particular reference to prescription wheelchair manufacturing. It will be appreciated, however, that the subject system is equally effective for fabrication of any body support member having a preselected contour.

The fitting seat or form means A has a generally horizontal or seat portion 10 pivotally connected by pivots 12 along one edge thereof to a generally vertical or back portion 14. The seat portion 10 has affixed thereto a deformable support cushion 16. Similarly, the back portion 14 has affixed thereto a deformable support cushion 18.

Both deformable seat cushions 16 and 18 are each suitably comprised of a generally air tight cover, 24 and 26 respectively. The covers 24 and 26 encase a deformable, air impregnated, medium such as a plurality of small, spherical pellets (not shown). The fitting seat A includes various support structures, each adapted with several degrees of freedom of motion for adjustment in accordance with a desirable orientation of a patient. Such an adjustment provides a means to achieve a desirable posture and/or force distribution of a patient.

With the relative connections and mountings illustrated by FIG. the following angles and orientations of the fitting seat A may be made. A seat height is adjustable by varying a vertical position of the seat portion 10 and the back portion 14 in relation to the support 28. This is accomplished by a height adjustment means 30, which is suitable comprised of a rachet-type, foot-actuated, piston assembly, as is illustrated. This provides the degree of freedom a, as is illustrated in the FIGURE.

A second degree of freedom of the fitting seat A is provided by the pivots 12, as noted above. Each pivot 12 is suitably comprised of a screw-type connector which includes a slotted support plate 34 which is rigidly mounted to vertical supports 36. Each slotted support plate 34 is slidably mounted to a horizontal support 38. Adjustment of the pivots 12 provides for variation of two degrees of freedom of the fitting seat A, namely pivotally along b or horizontally along c.

An additional degree of freedom is provided by varying an angle of the seat portion 10 to horizontal. This is suitably provided by a screw-type pivot, analogous to that illustrated at 12. Such a pivot has been eliminated from the figure for ease of illustration.

A foot support 42 includes a left foot support 44 and a right foot support 46. Description will be made herein solely for the right foot support 46, with the understanding that analogous structure is presented for the support 44. The right foot support 46 is slidably/pivotally mounted to a horizontal foot strut 48 via a mounting means suitably comprised of a thumb screw, a wing-nut, or the like. The mounting means 48, when loosened from the right foot support 46, provides for adjustment of the right foot support along the horizontal as illustrated at e, and pivotally, as illustrated at f.

The horizontal foot strut 48 is slidably mounted to a vertical foot strut 50, by a thumb screw, wing-nut, or the like. Loosening such fastening means provides for a degree of freedom of the right foot support generally along the vertical as illustrated in g.

An additional pivot means for the left foot support 44 and right foot support 46, with a degree of freedom illustrated at h, is provided by first and second pivotable mounting means extending between respective vertical foot struts 50 and the horizontal or seat portion 10. Such a pivot has been omitted from the subject figure for ease of illustration.

With the relative connections and mountings illustrated by FIG. the following angles and orientations of the fitting seat A may be made. These include: seat height, seat angle, back angle, seat depth, leg angle, leg length, and foot angle. While such degrees of freedom provide that which is generally desired for fitting of prescription seats, it will be appreciated by one of ordinary skill in the art that additional supports, and adjustments thereto, are often advantageous. Such might include means for positioning the arms of a patient at selected angles, or the provision of a selected head support.

With continuing reference to FIG. 1, the method by which a prescription seating has arrived at will be described. A patient is seated on the fitting seat A. A clinician adjusts the fitting seat to desirable parameters in relation to the particular patient. As part of the seating, the clinician varies the contour of the deformable support cushions 16 and 18 to acquire a desired weight distribution of a seated patient.

Such a weight distribution is arrived at subjectively, and is ideally sought for optimal support of a patient given his or her particular physical characteristics. Adjustment is also provided to minimize any compression points resultant from placement of unequal weight on one portion of the seated patient's body for long periods of time.

In the dilatency casting method, once desirable seating contours, dimensions, and angles have been arrived at, air is extracted from both the deformable seat cushions 16 and 18. As noted above, this is enabled by the provision of the respective air tight covers 24 and 26. The extraction of air from the support cushion 16 and 18 provides a semi-rigid form for fabrication of a prescription seat cushion.

Once the semi-rigid form of desirable cushion dimensions has been acquired in the system described above, a sensing means 60 is slidably mounted to first and second horizontal rails 62 and 64, as illustrated. For ease in reference, the fitting seat A is referenced with cartesian coordinates having x, y, and z, mutually-orthogonal, components or dimensions. Vertical is defined as a direction generally along the z axis, and horizontal is defined generally along the x-y plane. With this reference, the horizontal or seat portion 10 lies at, or at an angle to, the x-y plane. The back portion 14 lies on, or at an angle to, the x-z plane.

The sensing means 60 is comprised of a plurality of linear transducers 66. The sensing means 60 provide a means by which a cross-sectional signal representative of a generally two-dimensional cross-section of the seat portion 10 or back portion 14 of the form means A may be generated. Construction of the sensing means 60 will be described in more detail below.

The sensing means 60 communicates the cross-sectional signal to an analog-to-digital ("A/D") converter 72 which forms a digitized cross-sectional signal. Such a digitized cross-sectional signal is communicated to computer means B which, in the preferred embodiment, includes a video display terminal ("VDT") 74 and a mass-storage medium 76, illustrated as a plurality of disk drives. The computer means B provides a means for processing, storage, retrieval, and display of digitized data, as will be appreciated by one of ordinary skill in the art.

Data of the computer means B is selectively communicated to the communication interface C. In the preferred embodiment, the communications interface C includes a modulation/demodulation ("modem") unit 80. The modem 80 provides a means for modulating data for transmission via a carrier, such as along conventional telephone lines, radio, or the like.

Modulated data transmitted from the modem 80 is communicated to a receiving modem 84, which is included in the manufacturing D. Such data is demodulated by the modem 84, and selectively communicated to a fabrication means 86, the construction of which will be illustrated in more detail further below.

Figure 2:
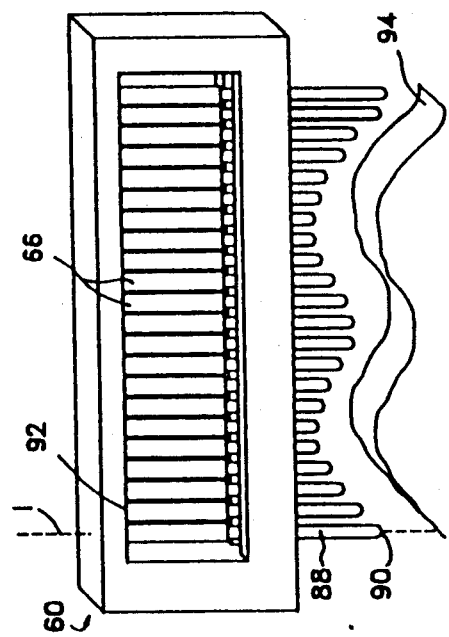
FIG. 2 illustrates the sensor array of FIG. 1.

Turning particularly to FIG. 2 and with continuing reference to FIG. 1, it will be seen that each linear transducer 66 is displaceable along a longitudinal axis 1 thereof. For ease in illustration, discussion will be had herein with regard to one transducer 88 of the plurality 66. It will be appreciated, however, that each transducer has similar structure. The longitudinal axis of each linear transducer 88 is generally parallel to corresponding longitudinal axes of each other longitudinal axis of each transducer of the array whereby a generally planar array is formed. Each linear transducer of the array 66 generates a signal representative of relative longitudinal displacement between its respective ends 90, 92. Such linear transducers are commonly available, and well within the understanding of one or ordinary skill in the art.

The sensing means 60 is perpendicularly mounted to the horizontal rails 62 and 64, such that each longitudinal axis of each linear transducer of the array 66 is generally perpendicular to the seat portion 10.

The sensing means 60 is comprised of a series of n transducers arranged in a generally planar configuration. Each transducer 88 is arranged such that a longitudinally displaceable end 90 thereof may be brought in contact with a surface area 94 for which a cross-sectional surface measurement is desired. The service area 94 is defined as a portion of one of the seat portion 10 or the back portion 14. When so disposed against the surface area portion 92, each transducer 88 of the array 60 generates a unique displacement signal therefrom. These signals, when combined, yield the cross-sectional signal from which a representation of the shape of surface area 92 is defined. The cross-sectional signal is formed by an amalgamation of displacement of individual transducers 88 along its longitudinal axis due to contact with the surface area 94, as well as information on relative displacement between transducers 88 of the array 66. Date points obtained by individual transducers 88 provides sufficient information to define a smooth or continuous surface by common, mathematical curve fitting techniques, as will be appreciated by one of ordinary skill in the art.

The transducer array 66 is progressed along a third dimension of the form means A in selected increments along a third dimension, defined by the plane of the sensing means 60. Another cross-sectional data reading is obtained after each such increment. Such a series of increments of the array 66 yields sufficient information to approximate the three-dimensional contour of both the seat portion 10 and the back portion 14.

Figure 3:
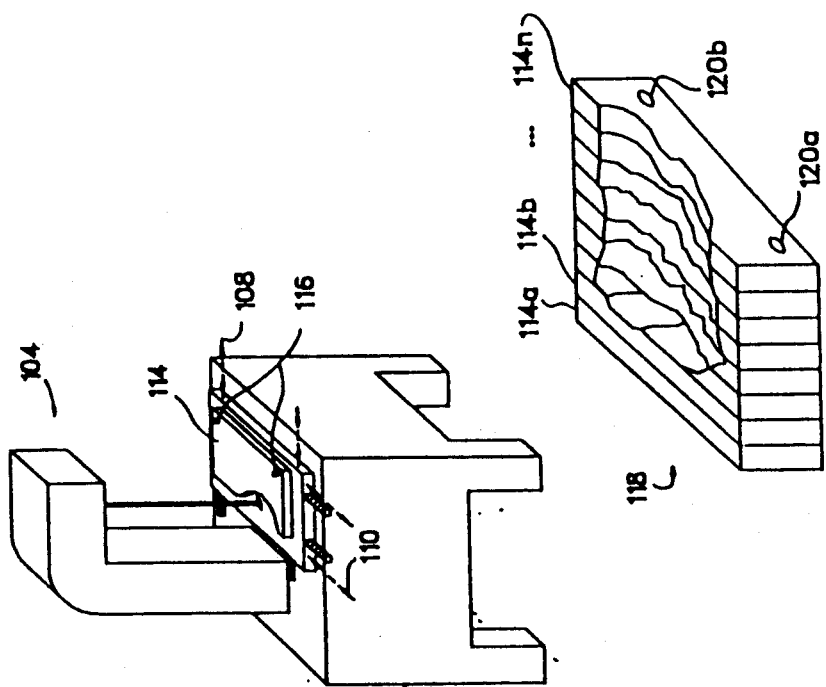
FIG. 3 illustrates a system for fabricating a prescription seat from data acquired from the system of FIG. 1; and, FIG. 4 illustrates a seat cushion constructed in accordance with the present invention.

Turning now to FIG. 3, the structure defining the fabrication means 86 will be described. Contour data representative of an entire three-dimensional surface such as the seat portion 10 or the back portion 14 is received from the computer means B into contour data receiver/decoder 100. This data is communicated, via interface 102, to a numerically-controlled ("NC") fabrication device or means, which is comprised of an NC milling machine, hot wire cutter, or the like.

The NC machine 102, in the preferred embodiment, includes a platter 106 having a planar moveability with mutually orthogonal degrees of freedom 108, 110.

A workpiece 114 is affixed to platter 106 by a means such as pins 116. The workpiece 114 preferably has a thickness corresponding to an increment at which the sensing means 60 was moved along the form means A during selected progressive measurements thereof. In the preferred embodiment, the workpiece 114 has a thickness generally about one-half inch.

Figure 4:
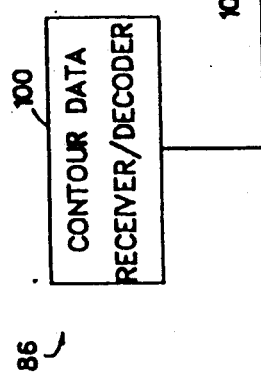

It will be appreciated by one of ordinary skill in the art that relative orientation of the platter 106 along its planar directions 108, 110, is readily dictatable by cross-sectional contour data generated by the sensing means 60. A series of workpieces 114 are sequentially placed in the numerically controlled machine 102, during which time they are cut corresponding to incremental cross-sectional signals. After a complete series of workpiece 114 has been fabricated, they are assembled in sequence to form a seat, such as that illustrated in FIG. 4, in which the series of workpieces 114a–114n, have been assembled. Such an assembly is suitably accomplished by fastening means 118 which are illustrated as rivets which traverse the length of a completed seat 118 through a hole created by pins 120a and 120b.

With the foregoing system, a prescription support system may be quickly fabricated either on-site, or off-site, with an increased accuracy.

The invention has been described with reference to the preferred embodiment. Obviously, modifications and alterations will occur to others upon the reading and understanding of the specification. It is intended that all such modifications and alterations are being included insofar as they come within the scope of the appended claims or the equivalents thereof.

Having thus described our invention, we now claim:

1. A contoured support fabrication unit comprising:
    a form means for defining a selected three-dimensional contour;
    sensing means for sensing a cross-sectional shape of first and second dimensions of the form means, the sensing means including means for generating a signal representative of the cross-sectional shape;
    stepper means for varying position of the sensing means along a remaining third dimension of the form means; and
    signal generator means for generating a cross-section signal representative of a cross-sectional shape sensed by the sensing means.

2. The fabrication unit of claim wherein the sensing means includes:
    a plurality of linear transducers, each linear transducer being displaceable along a longitudinal axis thereof; and
    securing means for securing the linear transducers in a generally linear array.

3. The fabrication unit of claim 2 wherein the securing means includes means for aligning the generally linear array such that each longitudinal axis is generally parallel to one another.

4. The fabrication unit of claim 3 further comprising means for obtaining a series of cross-section signals from selected displacements of the sensing means along the remaining third dimension of the form means.

5. The fabrication unit of claim 4 further comprising means for communicating the cross-sectional signal to a seat support fabrication means.

6. The fabrication unit of claim 5 wherein the fabrication means includes:
    stock securing means for securing stock;
    cutting means operatively connected to the stock securing means;
    means for controlling a position of the cutting means in relation to stock secured within the stock securing means in accordance with the cross-section signal.

7. The fabrication unit of claim 6 wherein the stepper means includes means for orienting, in generally equivalent increments, a position of the sensing means along the remaining third dimension of the form; and
    wherein the signal generator means includes means for generating a cross-section signal for each position of the sensing means along the remaining third dimension of form means.

8. The fabrication unit of claim 7 wherein the securing means includes means for sequentially securing a plurality of sheet stock portions thereto.

9. A method of contoured support fabrication comprising the steps of:
    sensing means for sensing a cross-sectional shape of first and second dimensions of a three-dimensional seat contour;
    varying position of the sensing means along a remaining third dimension of the three-dimensional contour; and
    generating a cross-section signal representative of a cross-sectional shape sensed by the sensing means.

10. The method of claim 9 further comprising the step obtaining a series of cross-section signals from selected displacements of the sensing means along the remaining third dimension of the three-dimensional contour.

11. The method of claim 10 further comprising the step of communicating the cross-sectional signal to a seat support fabrication means.

12. The method of claim 11 further comprising the steps of:
    securing stock to the seat support fabrication means;
    controlling a position of the cutting means in relation to stock secured within the securing means in accordance with the cross-section signal, whereby the stock is cut with a contour dictated by the cross-section signal.

13. The method of claim 12 including the steps of:
    stepping, in generally equivalent increments, a position of the sensing means along the remaining third dimension of the three-dimensional contour; and
    generating a cross-section signal for each position of the sensing means along the remaining third dimension of the three dimensional contour.

14. The method of claim 12 further comprising the steps of:
    sequentially securing at least one additional sheet stock portion to the seat support fabrication means; and
    controlling a position of the cutting means in accordance with the cross-section signal for the at least one additional stock portion.

15. The method of claim 14 further comprising the step of mounting each of the stock portions to one another such that a support closely matching dimensions of the three-dimensional seat contour is fabricated.

16. A prescription seat fabrication unit comprising:
    forming means for forming a three-dimensional contour representative of a surface portion of a seated patient, which contour is defined by first, second, and third mutually orthogonal axes;
    a plurality of linear transducers, each linear transducer being linearly displaceable along a longitudinal axis thereof;
    securing means for securing the plurality of linear transducers in a plane generally parallel to a plane defined by the first and second of the mutually orthogonal axes, such that each longitudinal axis is generally parallel to the first of the mutually orthogonal axes;

positioning means for positioning the securing means such that the plurality of linear transducers contact a three-dimensional contour formed by the forming means; and stepper means for varying a position of the positioning means along the third of the mutually orthogonal axes.

17. The prescription seat fabrication unit of claim 16 further comprising:

means for selectively receiving a displacement signal from each of the plurality of linear transducers, which signal is representative of displacement of each linear transducer about its respective longitudinal axis; and signal generator means combining each displacement signal to generate a cross-section signal representative of a cross-sectional shape of a three-dimensional contour formed by the forming means, which cross-sectional shape is defined generally along the first and second of the mutually orthogonal axes.

18. The prescription seat fabrication unit of claim 17 further comprising:

means for communicating the cross-section signal to a seat fabrication unit; and the seat fabrication unit including,
  cutting means; and
  stock positioning means for selectively positioning sheet stock in relation to the cutting means in accordance with the cross-section signal.

19. The prescription seat fabrication unit of claim 18 further comprising means for selectively receiving a plurality of sheet stock portions into the stock positioning means.

20. The prescription seat fabrication unit of claim 19 further comprising a means for securing the plurality of sheet portions to one another such that a seat resembling a three-dimensional contour formed by the forming means is fabricated.

* * * * *